(12) United States Patent
Kimura et al.

(10) Patent No.: US 6,720,463 B1
(45) Date of Patent: Apr. 13, 2004

(54) PROCESS FOR THE PRODUCTION OF ALKANEDIOL DERIVATIVE

(75) Inventors: Yoshikazu Kimura, Shizuoka (JP); Yukio Uchida, Shizuoka (JP); Shuichi Fujimoto, Shizuoka (JP)

(73) Assignee: Ihara Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 09/889,323

(22) PCT Filed: Nov. 16, 2000

(86) PCT No.: PCT/JP00/08066
§ 371 (c)(1),
(2), (4) Date: Jul. 13, 2001

(87) PCT Pub. No.: WO01/38276
PCT Pub. Date: May 31, 2001

(30) Foreign Application Priority Data

Nov. 19, 1999 (JP) ............................................. 11-330222

(51) Int. Cl.⁷ ......................... C07C 27/00; C07C 27/04; C07C 31/18
(52) U.S. Cl. ........................ 568/864; 568/626; 568/664; 568/665; 568/671; 568/672
(58) Field of Search ................................. 568/864, 672, 568/671, 626, 664, 665

(56) References Cited

U.S. PATENT DOCUMENTS 4,412,958 A * 11/1983 Cue, Jr. et al. .......... 260/456 R
5,981,809 A * 11/1999 Radisson .................... 568/864

FOREIGN PATENT DOCUMENTS

| JP | WO96/28405 | 9/1996 |
|---|---|---|
| JP | 10-507996 | 8/1998 |
| JP | WO99/44976 | 9/1999 |
| JP | 2000-226349 | 8/2000 |
| WO | WO 99/44976 | * 9/1999 |

* cited by examiner

Primary Examiner—Porfirio Nazario-Gonzalez
Assistant Examiner—Elvis O. Price
(74) Attorney, Agent, or Firm—Kubovcik & Kubovcik

(57) ABSTRACT

The present invention provides a process for producing an alkanediol derivative represented by the general formula (II) from an ester compound represented by the general formula (I), safely without giving rise to racemization.

The present invention lies in a process for producing an alcohol derivative represented by the following general formula (II):

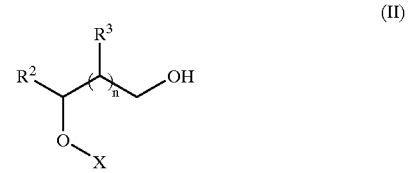

(II)

(wherein $R^2$ and $R^3$ are each independently a hydrogen atom or an alkyl group having 1 to 4 carbon atoms; X is a hydrogen atom or a protecting group for hydroxyl group; and n is 0 or 1), which process comprises reducing an ester compound represented by the following general formula (I):

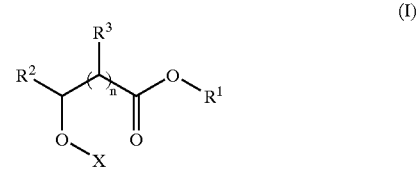

(I)

(wherein $R^1$ is an alkyl group having 1 to 4 carbon atoms; and $R^2$, $R^3$, X and n have the same definitions as given above) with sodium borohydride in a mixed solvent of at least one kind of solvent selected from the group consisting of aromatic hydrocarbons, aliphatic hydrocarbons and alicyclic hydrocarbons and a primary alcohol.

3 Claims, No Drawings

PROCESS FOR THE PRODUCTION OF ALKANEDIOL DERIVATIVE

This application is a 371 of PCT/JP00/08066, filed Nov. 16, 2000.

TECHNICAL FIELD

The present invention relates to a process for producing an alkanediol derivative.

BACKGROUND ART

Alkanediol derivatives represented by the following general formula (II):

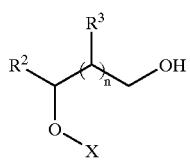

(II)

and, in particular, optically active (R)— or (S)-alkanediol derivatives are useful as a building block for agrochemical or pharmaceutical. For obtaining such a derivative, there has been known a process which comprises reducing a hydroxy carboxylic acid ester (e.g. an optically active 2-hydroxypropanoate or an optically active 3-hydroxybutanoate) or a compound obtained by protecting the hydroxyl group of the above ester with dihydropyran or the like, using lithium aluminum hydride or sodium bis(2-methoxyethoxy)aluminum hydride.

The above lithium aluminum hydride and sodium bis(2-methoxyethoxy)aluminum hydride, however, are difficult to handle in a large amount industrially from the safety standpoint. Therefore, active investigations have been made on a process for conducting the above-mentioned reduction using sodium borohydride which is easy to handle industrially.

However, it is generally impossible to reduce ester group to alcohol group using sodium borohydride [Tetrahedron, Vol.35, p.567 (1979)]. Hence, various reaction conditions have long been studied. For example, there were proposed a process which comprises conducting the reaction in the presence of a Lewis acid (e.g. aluminum chloride) [J. Am. Chem. Soc., Vol.78, p.2582 (1956)] and a process which comprises conducting the reaction in the presence of a metal salt (e.g. lithium chloride, lithium bromide or potassium bromide) [J. Am. Chem. Soc., Vol.77, p.6209 (1955)].

There were also proposed a process which comprises suspending sodium borohydride in tetrahydrofuran or tertiary butyl alcohol and slowly adding thereto a primary alcohol (e.g. methanol) under refluxing [Bull. Chem. Soc. Jpn., Vol.57, p.1948 (1984)], a process using a mixed solvent of an ether type solvent and a primary alcohol [Synlett., p.1636 (1999): WO 98/8793], a process using a polyethylene glycol as a solvent (JP-A-10-507996), a process using a mixed solvent of 1,2-dichloroethane and methanol (JP-A-1-250369), etc.

However, in obtaining an alkanediol derivative represented by the above general formula (II) by conducting reduction according to any of the above known processes, there are various problems. That is, for example, in the processes using a Lewis acid or a metal salt, the Lewis acid or the metal salt added results in an increase in the amount of waste material, which is not preferred; and in the process of dropwise adding a primary alcohol under refluxing, a large amount of hydrogen is generated rapidly when the process is carried out on a large scale, which is dangerous. In view of that solvent recovery is necessary in an industrial application of the above processes using a solvent, the process using an ether type solvent has a problem of requiring special facilities for ether separation from alcohol as well as for security against peroxide, and the use of 1,2-dichloroethane is restricted for its ozone depletion and global warming.

Thus, in the technical field to which the present invention belongs, no proposal has been made on a process for producing an alkanediol derivative represented by the general formula (II) safely without giving rise to racemization, and development of such a process has been desired.

The present invention aims at solving the above-mentioned problems and providing a novel and efficient process for producing an (R)—, (S)— or (RS)-alkanediol derivative which is useful as a building block.

DISCLOSURE OF THE INVENTION

In order to achieve the above aim, the present inventors made a study on a process for producing an alkanediol derivative represented by the general formula (II) by reducing a corresponding ester compound with sodium borohydride. As a result, it was found out surprisingly that the above ester compound is reduced with sodium borohydride at room temperature in a mixed solvent of a non-polar aprotic solvent, i.e. an aromatic hydrocarbon (e.g. chlorobenzene or toluene), an aliphatic hydrocarbon (e.g. hexane or heptane), an alicyclic hydrocarbon (e.g. cyclohexane or methylcyclohexane) or the like and a primary alcohol (e.g. methanol or ethanol) and is converted to an alkanediol derivative of the general formula (II) at a high yield without giving rise to racemization when the ester compound is optically active. The present invention has been completed based on the above finding. Incidentally, that the ester group of the ester compound is reduced to an alcohol with sodium borohydride at room temperature in a non-polar solvent with an addition of a primary alcohol, is an entirely novel finding which is far beyond the anticipation of those skilled in the art.

BEST MODE FOR CARRYING OUT THE INVENTION

The present invention is described in detail below.

The present invention provides the following inventions [1] and [2].

[1] A process for producing an alcohol derivative represented by the following general formula (II):

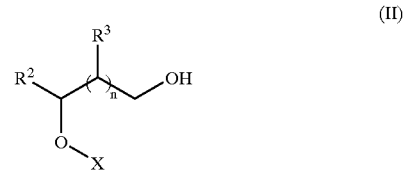

(II)

(wherein $R^2$ and $R^3$ are each independently a hydrogen atom or an alkyl group having 1 to 4 carbon atoms; X is a hydrogen atom or a protecting group for hydroxyl group; and n is 0 or 1), which process comprises reducing an ester compound represented by the following general formula (I):

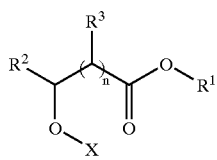

(wherein $R^1$ is an alkyl group having 1 to 4 carbon atoms; and $R^2$, $R^3$, X and n have the same definitions as given above) with sodium borohydride in a mixed solvent of at least one kind of solvent selected from the group consisting of aromatic hydrocarbons, aliphatic hydrocarbons and alicyclic hydrocarbons and a primary alcohol.

[2] A process according to the above [1], wherein the primary alcohol is methanol.

First, description is made on the ester compound represented by the general formula (I) which is used as a raw material in the present invention.

In the ester compound represented by the general formula (I) which is used as a raw material in the present process, the substituent represented by $R^1$ in the general formula (I) is an alkyl group having 1 to 4 carbon atoms, exemplified by methyl group, ethyl group, n-propyl group, isopropyl group, n-butyl group and isobutyl group; and the substituents represented by $R^2$ and $R^3$ are each independently a hydrogen atom or, similarly to $R^1$, an alkyl group having 1 to 4 carbon atoms.

The substituent represented by X in the general formula (I) is a hydrogen atom or a protecting group for hydroxyl group; and n is 0 or 1, indicating that the ester compound represented by the general formula (I) includes a compound wherein hydroxyl group is adjacent to carboxyl group and a compound wherein a carbon atom is present between hydroxyl group and carboxyl group.

Accordingly, as the ester compound represented by the general formula (I) wherein the substituent represented by X is a hydrogen atom, there can be mentioned, for example, methyl (R)-lactate, ethyl (R)-lactate, isobutyl (R)-lactate, methyl (S)-lactate, ethyl (S)-lactate, methyl (R)-3-hydroxybutanoate, methyl (S)-3-hydroxybutanoate and methyl (S)-3-hydroxy-2-methylpropionate or the like.

As the ester compound represented by the general formula (I) wherein the substituent represented by X is a protecting group for hydroxyl group, there can be mentioned, for example, compounds obtained by protecting the hydroxyl group of a compound represented by the general formula (I) wherein the substituent represented by X is a hydrogen atom, such as methyl (R)-lactate, ethyl (R)-lactate, isobutyl (R)-lactate, methyl (S)-lactate, ethyl (S)-lactate, methyl (R)-3-hydroxybutanoate, methyl (S)-3-hydroxybutanoate, methyl (S)-3-hydroxy-2-methylpropionate or the like, according to a conventional method.

The protecting group for hydroxyl group, used in the present invention is preferably a group which can be removed under an acidic condition, such as substituted methyl group, substituted ethyl group or the like. The substituted methyl group can be exemplified by methoxymethyl group (MOM) and 2-methoxyethoxymethyl (MEM) group, and the substituted ethyl group can be exemplified by tetrahydropyranyl group and ($C_{1-6}$ alkoxy)ethyl groups such as 1-ethoxyethyl group, 1-isobutoxyethyl group and the like.

The use of these protecting groups is described in detail in "Protective Groups in Organic Synthesis-3rd Edition, John Wiley & Sons, Inc. (1999)". In the present invention, by protecting hydroxyl group according to a conventional method described in the above literature, it is possible to obtain an ester compound represented by the general formula (I) wherein the substituent represented by X is a protecting group for hydroxyl group; it is also possible to remove, as necessary, the protecting group for hydroxyl group.

For example, a compound represented by the general formula (I) wherein the substituent represented by X is a substituted ethyl group, can be obtained by reacting a compound represented by the general formula (I) wherein the substituent represented by X is a hydrogen atom, with an alkyl vinyl ether in a solvent-free state or in an appropriate solvent in the presence of an acid catalyst.

The alkyl vinyl ether can be exemplified by dihydropyran, ethyl vinyl ether, propyl vinyl ether, isobutyl vinyl ether and cyclohexyl vinyl ether. These compounds are on the market and also available industrially.

As the acid catalyst, there are used organic acids such as camphorsulfonic acid, para-toluenesulfonic acid, trifluoroacetic acid and the like; inorganic acids such as sulfuric acid, hydrogen chloride and the like; pyridinium para-toluenesulfonate; phosphorous oxychloride; and so forth. The amount of the acid catalyst used is not critical but is 0.5 to 10 mole %, preferably 1 to 3 mole % relative to the compound represented by the general formula (I) wherein the substituent represented by X is a hydrogen atom.

As the solvent which may be used in the reaction for protection of hydroxyl group, there can be used any solvent which can dissolve the compound represented by the general formula (I) wherein the substituent represented by X is a hydrogen atom but does not react with the compound represented by the general formula (I) wherein the substituent represented by X is a hydrogen atom. There can be preferably mentioned, for example, aromatic, aliphatic or alicyclic hydrocarbon solvents such as toluene, xylene, cyclohexane, methylcyclohexane, octane, heptane and the like. The amount of the solvent used is not restricted but is 0.3 to 2.0 liters, preferably 0.5 to 1.5 liters per mole of the compound represented by the general formula (I) wherein the substituent represented by X is a hydrogen atom.

Next, description is made on the process of the present invention wherein an ester compound represented by the general formula (I) is reduced to an alkanediol derivative represented by the general formula (II).

The reaction of the present process can be conducted simply by mixing an ester compound represented by the general formula (I), sodium borohydride and a solvent and stirring the resulting mixture. There is no particular restriction as to the addition order of these substances.

The solvent used in the above reaction is a mixed solvent of at least one kind selected from the group consisting of aromatic hydrocarbons, aliphatic hydrocarbons and alicyclic hydrocarbons and a primary alcohol.

As the aromatic hydrocarbons, there can be mentioned, for example, chlorobenzene, toluene, 4-chlorotoluene, 2-chlorotoluene, 2,4-dichlorotoluene, naphthalene and 1-chloronaphthalene; as the aliphatic hydrocarbons, there can be mentioned, for example, pentane, hexane, heptane, octane and isooctane; and as the alicyclic hydrocarbons, there can be mentioned, for example, cyclohexane and methylcyclohexane.

The solvent selected from the group consisting of aromatic hydrocarbons, aliphatic hydrocarbons and alicyclic hydrocarbons can be one kind or two or more kinds (in this case, there is no particular restriction as to their mixing proportions). The amount of the solvent used is not particularly restricted and is 0.3 to 2.0 liters, preferably 0.5 to 1.5 liters per mole of the ester compound represented by the general formula (I).

As the primary alcohol to be mixed with the above hydrocarbon solvent to constitute a mixed solvent used in the above-mentioned reaction, there can be mentioned, for example, methanol and ethanol. Methanol is preferred for the high reaction rate. The primary alcohol is used in an amount of 3 to 12 equivalents, preferably 5 to 8 equivalents relative to the ester compound represented by the general formula (I); however, the amount used is not restricted thereto.

Meanwhile, the amount of sodium borohydride used is 1 to 6 equivalents, preferably 1 to 3 equivalents, more preferably 1.3 to 2.0 equivalents relative to the ester compound represented by the general formula (I); however, the amount used is not restricted thereto.

The above reaction proceeds smoothly at a reaction temperature of 0 to 80° C., preferably 20 to 40° C. and, in particular, stirring at room temperature is simple and gives a high yield.

In the reaction of the present process, there can be employed various specific procedures; for example, a procedure in which an ester compound represented by the general formula (I) and sodium borohydride are suspended or dissolved in toluene, methanol is added dropwise thereto at room temperature, and, in this state, stirring is conducted up to the completion of a reaction, or a procedure in which a methanol solution of an ester compound represented by the general formula (I) is added at room temperature to a toluene suspension of sodium borohydride.

After the completion of the reaction, the reaction product is isolated by an ordinary extraction operation and purified by distillation, or water is added to the reaction mixture to remove the alcohol so that the reaction product dissolved in toluene can be used per se in the next reaction.

Of the ester compounds represented by the general formula (I), the alkoxyethyl group-protected (R)— or (S)-propionic acid esters represented by the following general formula (III), excluding some compounds, are not described in Chemical Abstract and are novel compounds whose properties are unknown.

(III)

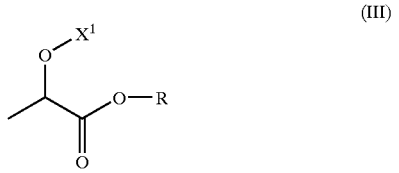

[wherein $X^1$ is a ($C_{1-6}$ alkoxy)ethyl group, and R has the same definition as the above-mentioned $R^1$].

As such novel ($C_{1-6}$ alkoxy)ethyl group-protected (R)— or (S)-propionic acid esters represented by the general formula (III), there can be specifically mentioned, for example, isobutyl (R)-2-(1-ethoxyethoxy)propionate, isobutyl (R)-2-(1-isobutoxyethoxy)propionate, methyl (R)-2-(1-isobutoxyethoxy)propionate, isobutyl (R)-2-(1-n-butoxyethoxy)propionate and isobutyl (R)-2-(1-cyclohexyloxyethoxy)propionate.

The alkoxyethyl group used as a protecting group for hydroxyl group in the compound represented by the general formula (III), as compared with tetrahydropyranyl group, is removable under milder conditions and therefore is known to hardly cause racemization in the reaction for protecting group removal in optically active compound. In, for example, S. Chladek and J. Smrt., Chem. & Ind. (London), 1719 (1964), it is described that while racemization takes place partially in the removal of tetrahydropyranyl group, no racemization takes place in the removal of ethoxyethyl group.

Of the alkanediol derivatives represented by the general formula (II), the 1,2-propanediol derivatives represented by the following general formula (IV), other than some compounds, are novel compounds not described in Chemical Abstract.

(IV)

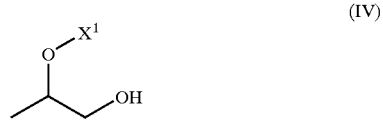

(wherein $X^1$ has the same definition as given above)

As such novel 1,2-propanediol derivatives represented by the general formula (IV), there can be specifically mentioned, for example, (R)-2-(1-isobutoxyethoxy)-1-propanol, (S)-2-(1-isobutoxyethoxy)-1-propanol, (R)-2-(1-n-butoxyethoxy)-1-propanol and (R)-2-(1-cyclohexyloxyethoxy)-1-propanol.

Hereinafter, the process of the present invention is described more specifically by way of Examples and Reference Examples.

REFERENCE EXAMPLE 1

Isobutyl (R)-(+)-2-[(Tetrahydro-2H-pyran-2-yl)oxy] propionate 21.8 g (0.26 mole) of 3,4-dihydro-2H-pyran was dropwise added at room temperature to a mixture of 29.2 g (0.2 mole) of isobutyl (R)-(+)-lactate and 0.3 g of phosphorus oxychloride. After the completion of the dropwise addition, the resulting mixture was stirred at room temperature for 4 hours. After the reaction, 100 ml of ethyl acetate was added, followed by washing with 70 ml of a saturated aqueous sodium hydrogen carbonate solution, 70 ml of water and 70 ml of a saturated aqueous sodium chloride solution in this order. The washed material was dried over anhydrous sodium sulfate and then subjected to vacuum distillation to remove the solvent, whereby was obtained 49.0 g (yield: 92.1%) of an oily title compound (diastereomixture).

Boiling point: 79.2–80.5° C. (106.6–159.9 Pa); $[\alpha]_D^{24.8}$=+58.6° (c=1.85, CHCl$_3$); $^1$H-NMR (300 MHz, CHCl$_3$-d$_1$), δ=0.94, 0.95 (d, J=6.6 Hz, 6H), 1.41, 1.47 (d, J=6.9 Hz, 3H), 1.5–2.0 (m, 7H), 3.4–3.6 (m, 1H), 3.8–4.0 (m, 3H), 4.22 (q, J=6.9 Hz, 0.5H), 4.44 (q, J=6.9 Hz, 0.5H), 4.7–4.8 (m, 1H); IR (neat): 1751 cm$^{-1}$ (CO); MS (GC–MS) m/e=229 (M$^+$–1), 85 (base).

EXAMPLE 1

(R)-(+)-2-[(Tetrahydro-2H-pyran-2-yl)oxy]-1-propanol 34.5 g (0.15 mole) of the isobutyl (R)-(+)-2-[(tetrahydro-2H-pyran-2-yl)oxy]propionate obtained in Reference Example 1 and 8.5 g (0.225 mole) of sodium borohydride were suspended in 100 ml of chlorobenzene. Thereto was dropwise added slowly 49 ml of methanol with stirring while the internal temperature of the reaction system was kept at 36° C. or less. The resulting solution was stirred at room temperature for 22 hours. After the reaction, the reaction mixture was washed with 50 ml of water (twice) and 50 ml of a saturated aqueous sodium chloride solution in this order. The washed material was dried over anhydrous sodium sulfate and then subjected to vacuum distillation to remove the solvent. The resulting concentrate was subjected to distillation to obtain 24.2 g (yield: 99.8%) of an oily title compound (diastereomixture).

Boiling point: 64.9–68.2° C. (65.3–73.3 Pa); $[\alpha]_D^{24.8}$=+ 10.1° (c=2.26, CHCl$_3$); $^1$H-NMR (300 MHz, CHCl$_3$-d$_1$), δ=1,14, 1.22 (d, J=6.5 Hz, 3H), 1.5–1.9 (m, 6H), 2.1–2.2 (m, 1H), 3.4–3.7 (m, 3H), 3.8–4.0 (m, 2H), 4.5–4.6 (m, 0.5H), 4.7–4.8 (m, 0.5H); IR (neat): 3439 cm$^{-1}$ (OH); MS (GC-MS) m/e=159 (M$^+$-1), 85 (base).

REFERENCE EXAMPLE 2

Methyl (R)-(+)-2-(1-Ethoxyethoxy)propionate

A catalytic amount of pyridinium para-toluenesulfonate was added to 20.8 g (0.2 mole) of methyl (R)-(-+)-lactate (98.9% e.e) and 18.7 g (0.26 mole) of ethyl vinyl ether. The resulting mixture was stirred at room temperature for 6 hours. After the reaction, thereto was added 100 ml of ethyl acetate, followed by washing with 70 ml of a saturated aqueous sodium hydrogen carbonate solution, 70 ml of water and 70 ml of a saturated aqueous sodium chloride solution in this order. The washed material was dried over anhydrous sodium sulfate and then subjected to vacuum distillation to remove the solvent. The resulting concentrate was subjected to distillation to obtain 49.0 g (yield: 97.8%) of an oily title compound (diastereomixture).

Boiling point: 36.0–38.2° C. (46.7–66.6 Pa); $[\alpha]_D^{24.2}$=+ 82.4° (c=10.03, CHCl$_3$); $^1$H-NMR (300 MHz, CHCl$_3$-d$_1$), δ=1.16, 1.18 (t, J=7.0 Hz, 3H), 1.32, 1.36 (d, J=5.4 Hz, 3H), 1.23, 1.40 (d, J=6.9 Hz, 3H), 3.5–3.7 (m, 2H), 3.74 (s, 3H), 4.20–4.36 (q, J=6.9 Hz, 1H), 4.77 (q, 1H, J=5.4 Hz); IR (neat): 1754 cm$^{-1}$ (CO); MS (GC-MS) m/e=175 (M$^+$-1), 73 (base).

EXAMPLE 2

(R)-(-)-2-(1-Ethoxyethoxy)-1-propanol 26.4 g (0.15 mole) of the methyl (R)-(+)-2-(1-ethoxyethoxy)propionate obtained in Reference Example 2 and 8.5 g (0.225 mole) of sodium borohydride were added to 70 ml of chlorobenzene. Thereto was dropwise added 14 ml of methanol while the internal temperature of the reaction system was kept at 35° C. The resulting solution was stirred at room temperature for 4 hours. After the reaction, the reaction mixture was washed with 50 ml of water (twice) and 50 ml of a saturated aqueous sodium chloride solution in this order.

The washed material was dried over anhydrous sodium sulfate and then subjected to vacuum distillation to remove the solvent. The resulting concentrate was subjected to distillation to obtain 22.4 g (yield: 99.8%) of an oily title compound (diastereomixture). Part of the compound was subjected to an acid treatment to convert to (R)-1,2-propanediol, and its optical purity was measured using a high performance liquid chromatography (HPLC) with an optically active column. The optical purity was 98.9% e.e.

Boiling point: 40.0–42.0° C. (65.3–73.3 Pa); $[\alpha]_D^{24.0}$=-40.6° (c=2.91, CHCl$_3$); $^1$H-NMR (300 MHz, CHCl$_3$-d$_1$); δ=0.94 (d, J=6.6 Hz, 6H), 1.17, 1.19 (t, J=7.0 Hz, 3H), 1.31, 1.37 (d, J=5.1 Hz, 3H), 1.43 (d, J=6.9 Hz, 3H), 1.9–2.0 (m, 1H), 3.5–3.7 (m, 2H), 3.9–4.0 (m, 2H), 4.22, 4.36 (q, 6.9 Hz, 1H), 4.79, 4.80 (q, J=5.1 Hz, 1H); IR (neat): 3433 cm$^{-1}$ (OH); MS (GC-MS) m/e=147 (M$^+$-1), 73 (base).

REFERENCE EXAMPLE 3

Isobutyl (R)-(+)-2-(1-Ethoxyethoxy)propionate 17.2 g of dehydrated ethyl vinyl ether was dropwise added to a mixture of 32.7 g of isobutyl (R)-(+)-lactate and 0.3 g of phosphorus oxychloride which was being stirred at room temperature, so that the internal temperature of the reaction system could be kept at 40° C. or less. Then, the resulting mixture was stirred at room temperature overnight. After the reaction, thereto was added 200 ml of ethyl acetate, followed by washing with a saturated aqueous sodium hydrogen carbonate solution, water and a saturated aqueous sodium chloride solution in this order. The washed material was dried over anhydrous sodium sulfate and then subjected to vacuum distillation to remove the solvent. The resulting concentrate was subjected to distillation to obtain 40.1 g (yield: 91.8%) of an oily title compound (diastereomixture).

Boiling point: 57.0° C. (26.7 Pa); $[\alpha]_D^{24.0}$=+78.8° (c=1.16, CHCl$_3$); $^1$H-NMR (300 MHz, CHCl$_3$-d$_1$); δ=0.94 (d, J=6.6 Hz, 6H), 1.17, 1.19 (t, J=7.0 Hz, 3H), 1.31, 1.37 (d, J=5.1 Hz, 3H), 1.43 (d, J=6.9 Hz, 3H), 1.9–2.0 (m, 1H), 3.5–3.7 (m, 2H), 3.9–4.0 (m, 2H), 4.22, 4.36 (q, J=6.9 Hz, 1H), 4.79, 4.80 (q, J=5.1 Hz, 1H); IR (neat): 1752 cm$^{-1}$ (CO); MS (GC-MS) m/e=217 (M$^+$-1), 73 (base).

EXAMPLE 3

(R)-(-)-2-(1-Ethoxyethoxy)-1-propanol 1.85 g of sodium borohydride was suspended at room temperature in a solution of 7.52 g of the isobutyl (R)-(+)-2-(1-ethoxyethoxy)propionate (obtained in Reference Example 3) dissolved in 30 ml of chlorobenzene. Thereto was dropwise added slowly 7.3 ml of methanol with stirring, so that the internal temperature of the reaction system could be kept at 40° C. After the completion of the dropwise addition, the mixture was stirred at room temperature for 5 hours. to give rise to a reaction. After the reaction, thereto was added 60 ml of water, followed by extraction with 120 ml of ethyl acetate. The water layer was subjected to extraction with 60 ml of ethyl acetate. The two organic layers were combined and washed with a saturated aqueous sodium chloride solution. The washed solution was dried over anhydrous sodium sulfate and then subjected to vacuum distillation to remove the solvent. The resulting concentrate was subjected to distillation to obtain 4.0 g (yield: 90.8%) of an oily title compound (diastereomixture).

Boiling point: 31.0° C. (53.3 Pa); $[a]_D^{24.0}$=-46.5° (c=1.04, CHCl$_3$).

The IR, NMR and MS spectrum were identical with those of the compound obtained in Example 2.

REFERENCE EXAMPLE 4

Isobutyl (R)-(+)-2-(1-Isobutoxyethoxy)propionate 24.0 g of dehydrated isobutyl vinyl ether was dropwise added to a mixture of 32.7 g of isobutyl (R)-(+)-lactate and 0.3 g of phosphorus oxychloride which was being stirred at room temperature, so that the internal temperature of the reaction system could be kept at 40° C. or less. Then, the resulting mixture was stirred at room temperature overnight. After the reaction, thereto was added 200 ml of ethyl acetate, followed by washing with a saturated aqueous sodium hydrogen carbonate solution, water and a saturated aqueous sodium chloride solution in this order. The washed material was dried over anhydrous sodium sulfate and then subjected to vacuum distillation to remove the solvent. The resulting concentrate was subjected to distillation to obtain 47.8 g (yield: 96.9%) of an oily title compound (diastereomixture).

Boiling point: 63.0° C. (40.0 Pa); $[\alpha]_D^{24.0}$=+80.7° (c=1.01, CHCl$_3$); 1H-NMR (300 MHz, CHCl$_3$-d$_1$); δ=0.89, 0.91 (d, J=6.3 Hz, 6H), 0.90, 0.94 (d, J=6.6 Hz, 6H), 1.31, 1.36 (d, J=5.4 Hz, 3H), 1.40, 1.43 (d, J=6.9 Hz, 3H), 1.8–1.9 (m, 1H), 1.9–2.0 (m, 1H), 3.2–3.4 (m, 2H), 3.9–4.0 (m, 2H), 4.24, 4.38 (q, J=6.9 Hz, 1H), 4.78 (q, J=5.4 Hz, 1H); IR (neat): 1753 cm$^{-1}$ (CO); MS (GC–MS) m/e=245 (M$^{+}$–1), 57 (base).

EXAMPLE 4

(R)-(−)-2-(1-Isobutoxyethoxy)-1-propanol 5.7 g of sodium borohydride was suspended at room temperature in a solution of 25.0 g of the isobutyl (R)-(+)-2-(1-isobutoxyethoxy)propionate (obtained in Reference Example 4) dissolved in 30 ml of cyclohexane. Thereto was dropwise added slowly 24 ml of methanol with stirring, so that the internal temperature of the reaction system could be kept at 40° C. After the completion of the dropwise addition, the mixture was stirred at room temperature for 5 hours. After the reaction, the reaction mixture was added 100 ml of water, followed by stirring for a while. Thereto was added 200 ml of ethyl acetate. The resulting organic layer was separated, washed with a saturated aqueous sodium chloride solution, and dried over anhydrous sodium sulfate. The resulting solution was subjected to vacuum distillation to remove the solvent. The resulting concentrate was subjected to distillation to obtain 17.3 g (yield: 98.0%) of an oily title compound (diastereomixture).

Boiling point: 43.0° C. (40.0 Pa); $[\alpha]_D^{24.0}$=−44.5° (c=1.11, CHCl$_3$); $^1$H-NMR (300 MHz, CHCl$_3$-d$_1$); δ=0.92 (d, J=6.9 Hz, 6H), 1.12, 1.18 (d, J=6.3 Hz, 3H), 1.33, 1.35 (d, J=5.4 Hz, 3H), 1.8–1.9 (m, 1H), 2.35 (dd, J=4.5, 7.8 Hz, 0.5H), 3.07 (dd, 3.6, 8.7 Hz, 0.5H), 3.2–3.3 (m, 2H), 3.4–3.6 (m, 2H), 3.8–3.9 (m, 1H), 4.71, 4.79 (q, J=5.4 Hz, 1H); IR (neat): 3448 cm$^{-1}$ (OH); MS (GC–MS) m/e=175 (M$^{+}$–1), 57 (base).

EXAMPLES 5–12

7.52 g of isobutyl (R)-(+)-2-(1-ethoxyethoxy)propionate was reacted with 1.85 g (1.5 eq) of sodium borohydride in the same manner as in Example 3 with the solvent and reaction temperature changed as shown in Table 1. The yield of each product was measured by GC (gas chromatography). The results are shown in Table 1. Incidentally, "eq" refers to "equivalent" and "h" refers to "hour(s)".

Reduction to (R)-(−)-2-(1-Ethoxyethoxy)-1-propanol (IIa)

TABLE 1

| Ex. | Solvent (1 litter/ mole) | Additive (relative to raw material) | Temp. | Reaction time | Yield of IIa (%) |
|---|---|---|---|---|---|
| 5 | Chlorobenzene | Methanol 6 eq | Room temp. | 7 h | 99.3 |
| 6 | Chlorobenzene | Methanol 6 eq | 40° C. | 5 h | 98.7 |
| 7 | Chlorobenzene | Methanol 6 eq | 60° C. | 6 h | 78.2 |
| 8 | Chlorobenzene | Methanol 3 eq | 40° C. | 5 h | 67.0 |
| 9 | Chlorobenzene | Methanol 12 eq | 40° C. | 5 h | 92.5 |
| 10 | Chlorobenzene | Ethanol 6 eq | 60° C. | 6 h | 30.6 |
| 11 | Toluene | Methanol 6 eq | Room temp. | 7 h | 94.1 |
| 12 | Cyclohexane | Methanol 6 eq | Room temp. | 5 h | 99.4 |

EXAMPLE 13

(R)-(−)-2-(1-Isobutoxyethoxy)-1-propanol 2.5 g of sodium borohydride was suspended at room temperature in a solution of 12.3 g of isobutyl (R)-(+)-2-(1-isobutoxyethoxy)propionate dissolved in 50 ml of toluene. Thereto was dropwise added slowly 14.4 g of methanol with stirring, so that the internal temperature of the reaction system could be kept at 34° C. or less. After the completion of the dropwise addition, the resulting mixture was stirred at room temperature for 4.5 hours. After the reaction, the reaction mixture was added 30 ml of water, followed by stirring for a while. The resulting organic layer was separated, washed with a saturated aqueous sodium chloride solution, and dried over anhydrous sodium sulfate. The resulting solution was subjected to vacuum distillation to remove the solvent, whereby was obtained 8.4 g (yield: 96%) of an oily title compound (diastereomixture). This compound was identical with the compound obtained in Example 4.

REFERENCE EXAMPLE 5

Methyl (R)-(+)-2-(1-Isobutoxyethoxy)propionate

A catalytic amount of pyridinium para-toluenesulfonate was added to 20.8 g (0.2 mole) of methyl (R)-(+)-lactate and 22.0 g (0.22 mole) of isobutyl vinyl ether. The resulting mixture was stirred at room temperature for 3 hours to give rise to a reaction. Thereto was added 100 ml of ethyl acetate, followed by washing with 100 ml of a saturated aqueous sodium hydrogen carbonate solution, 40 ml of water and 40 ml of a saturated aqueous sodium chloride solution in this order. The washed material was dried over anhydrous sodium sulfate and then subjected to vacuum distillation to remove the solvent. The resulting concentrate was subjected to distillation to obtain 38.8 g (yield: 95.1%) of an oily title compound (diastereomixture).

Boiling point: 43° C. (53.3 Pa); $[\alpha]_D^{24.2}$:+80.0° (c=1.05, CHCl$_3$); $^1$H-NMR (300 MHz, CHCl$_3$-d$_1$); δ=0.8–0.9 (m, 6H), 1.31, 1.35 (d, J=5.4 Hz, 3H), 1.39, 1.42 (d, J=6.9 Hz, 3H), 1.7–1.8 (m, 1H), 3.2–3.4 (m, 2H), 3.74 (s, 3H), 4.24, 4.38 (q, J=6.9 Hz, 1H), 4.77 (q, J=5.4 Hz, 1H); IR (neat): 1755 cm$^{-1}$ (CO); MS (GC–MS) m/e: 203 (M$^{+}$–1), 59 (base).

EXAMPLE 14

(R)-(−)-2-(1-Isobutoxyethoxy)-1-propanol 8.4 g (0.204 mole) of sodium borohydride was suspended at room temperature in a solution of 35.8 g (0.17 mole) of the methyl (R)-(+)-2-(1-isobutoxyethoxy)propionate (obtained in Reference Example 5) dissolved in 170 ml of toluene. Thereto was dropwise added slowly 40.8 ml (1.02 mole) of methanol with stirring, so that the internal temperature of the reaction system could be kept at 40° C. After the completion of the dropwise addition, the mixture was stirred at room temperature for 4 hours to give rise to a reaction. To the reaction mixture was added 50 ml of water, followed by stirring for 0.5 hour. The organic layer was separated. The water layer was subjected to re-extraction with 50 ml of toluene. The two organic layers were combined and washed with 50 ml of water and 50 ml of a saturated aqueous sodium chloride solution in this order. The washed solution was dried over anhydrous sodium sulfate and then subjected to vacuum distillation to remove the solvent. The resulting concentrate was subjected to distillation to obtain 28.9 g (yield: 98.0%) of an oily title compound (diastereomixture).

Boiling point: 47.0° C. (80.0 Pa); $[\alpha]_D^{24.0}$: −37.0° (c=1.05, CHCl$_3$).

The IR, NMR and MS spectrum were identical with those of the compound obtained in Example 4.

REFERENCE EXAMPLE 6

Isobutyl (R)-(+)-2-(1-n-Butoxyethoxy)propionate

A catalytic amount of pyridinium para-toluenesulfonate was added to 29.2 g (0.2 mole) of isobutyl (R)-(+)-lactate and 22.0 g (0.22 mole) of n-butyl vinyl ether. The resulting mixture was stirred at room temperature for 4 hours to give rise to a reaction. Thereto was added 100 ml of ethyl acetate, followed by washing with 100 ml of a saturated aqueous sodium hydrogen carbonate solution, 40 ml of water and 40 ml of a saturated aqueous sodium chloride solution in this order. The washed material was dried over anhydrous sodium sulfate and then subjected to vacuum distillation to remove the solvent, whereby was obtained 46.8 g (yield: 94.9%) of an oily title compound (diastereomixture).

Boiling point: 67° C. (26.7 Pa); $[\alpha]_D^{24.2}$: +79.2° (c=1.04, CHCl$_3$); $^1$H-NMR (300 MHz, CHCl$_3$-d$_1$), δ: 0.9–1.0 (m, 9H), 1.3–1.6 (m, 10H), 1.9–2.0 (m, 1H), 3.4–3.7 (m, 2H), 3.9–4.0 (m, 2H), 4.22, 4.36 (q, J=6.9 Hz, 1H), 4.78 (q, J=5.4 Hz, 1H); IR (neat): 1753 cm$^{-1}$ (CO); MS (GC–MS) m/e: 245 (M$^+$–1), 101 (base).

EXAMPLE 15

(R)-(–)-2-(1-n-Butoxyethoxy)-1-propanol 8.4 g (0.204 mole) of sodium borohydride was suspended at room temperature in a solution of 44.1 g (0.17 mole) of the isobutyl (R)-(+)-2-(1-n-butoxyethoxy)propionate (obtained in Reference Example 6) dissolved in 170 ml of toluene. Thereto was dropwise added slowly 41.3 ml (1.02 mole) of methanol with stirring, so that the internal temperature of the reaction system could be kept at 40° C. After the completion of the dropwise addition, the resulting mixture was stirred at room temperature for 5 hours to give rise to a reaction. To the reaction mixture was added 50 ml of water, followed by stirring for 0.5 hour. The organic layer was separated. The water layer was subjected to extraction with 50 ml of toluene. The two organic layers were combined and washed with 50 ml of water and 50 ml of a saturated aqueous sodium chloride solution in this order. The washed solution was dried over anhydrous sodium sulfate and then subjected to vacuum distillation to remove the solvent, whereby was obtained 27.4 g (yield: 91.3%) of an oily title compound (diastereomixture).

Boiling point: 51.0° C. (53.3 Pa); $[\alpha]_D^{24.0}$: –45.8° (c=1.09, CHCl$_3$); $^1$H-NMR (300 MHz, CHCl$_3$-d$_1$), δ: 0.93, 0.95 (t, J=7.2 Hz, 3H), 1.12, 1.17 (d, J=6.3 Hz, 3H), 1.34, 1.35 (d, J=5.4 Hz, 3H), 1.3–1.4 (m, 2H), 1.5–1.6 (m, 2H), 2.44 (dd, J=4.5, 7.8 Hz, 0.5H), 3.17 (dd, J=3.3, 9.0 Hz, 0.5H), 3.4–3.7 (m, 4H), 3.8–3.9 (m, 1H), 4.71, 4.79 (q, J=5.4 Hz, 1H); IR (neat): 3448 cm$^{-1}$ (OH); MS (GC–MS) m/e: 175 (M$^+$–1), 59 (base).

REFERENCE EXAMPLE 7

Isobutyl (R)-(+)-2-(1-Cyclohexyloxyethoxy)propionate

A catalytic amount of pyridinium para-toluenesulfonate was added to 29.2 g (0.2 mole) of isobutyl (R)-(+)-lactate and 28.0 g (0.22 mole) of cyclohexyl vinyl ether. The resulting mixture was stirred at room temperature for 4 hours to give rise to a reaction. Thereto was added 100 ml of ethyl acetate, followed by washing with 100 ml of a saturated aqueous sodium hydrogen carbonate solution, 40 ml of water and 40 ml of a saturated aqueous sodium chloride solution in this order. The washed material was dried over anhydrous sodium sulfate and then subjected to vacuum distillation to remove the solvent, whereby was obtained 54.2 g (yield: 99.4%) of an oily title compound (diastereomixture).

Boiling point: 90° C. (40.0 Pa); $[\alpha]_D^{24.2}$: +100.6° (c=1.34, CHCl$_3$); $^1$H-NMR (300 MHz, CHCl$_3$-d$_1$), δ: 0.95 (d, J=6.6 Hz, 6H), 1.2–1.3 (m, 6H), 1.35, 1.37 (d, J=5.1 Hz, 3H), 1.39, 1.42 (d, J=6.9 Hz, 3H), 1.7–1.8 (m, 4H), 1.9–2.0 (m, 1H), 3.4–3.6 (m, 1H), 3.9–4.0 (m, 2H), 4.26, 4.38 (q, J=6.9 Hz, 1H), 4.84, 4.91 (q, J=5.1 Hz, 1H); IR (neat): 1752 cm$^{-1}$ (CO); MS (GC–MS) m/e: 257, 127 (base).

EXAMPLE 16

(R)-(–)-2-(1-Cyclohexyloxyethoxy)-1-propanol 8.4 g (0.204 mole) of sodium borohydride was suspended at room temperature in a solution of 47.9 g (0.17 mole) of the isobutyl (R)-(+)-2-(1-cyclohexyloxyethoxy)propionate (obtained in Reference Example 7) dissolved in 170 ml of toluene. Thereto was dropwise added slowly 41.3 ml (1.02 mole) of methanol with stirring, so that the internal temperature of the reaction system could be kept at 40° C. After the completion of the dropwise addition, the resulting mixture was stirred at room temperature for 7 hours to give rise to a reaction. To the reaction mixture was added 50 ml of water, followed by stirring for 0.5 hour. The organic layer was separated. The water layer was subjected to extraction with 50 ml of toluene. The two organic layers were combined and washed with 50 ml of water and 50 ml of a saturated aqueous sodium chloride solution in this order. The washed solution was dried over anhydrous sodium sulfate and then subjected to vacuum distillation to remove the solvent, whereby was obtained 30.5 g (yield: 88.7%) of an oily title compound (diastereomixture).

Boiling point: 76.0° C. (53.3 Pa); $[\alpha]_D^{24.0}$: –57.6° (c=0.89, CHCl$_3$); $^1$H-NMR (300 MHz, CHCl$_3$-d$_1$), δ: 1.12, 1.16 (d, J=6.6 Hz, 3H), 1.2–1.3 (m, 4H), 1.34, 1.35 (d, J=5.1 Hz, 3H), 1.5–1.6 (m, 2H), 1.7–1.8 (m, 2H), 1.8–1.9 (m, 2H), 2.78 (dd, J=4,5, 8.1 Hz, 0.5H), 3.21 (dd, J=3.3, 9.0 Hz, 0.5H), 3.5–3.6 (m, 3H), 3.7–3.9 (m, 1H), 4.76 (q, J=5.1 Hz, 0.5H), 4.89 (q, J=5.4 Hz, 0.5H); IR (neat): 3448 cm$^{-1}$ (OH); MS (GC–MS) m/e: 187, 59 (base).

EXAMPLE 17

(R)-(–)-2-(1-Isobutoxyethoxy)-1-propanol 1.0 g (0.024 mole) of sodium borohydride was suspended at room temperature in a solution of 5.0 g (0.02 mole) of isobutyl (R)-(+)-2-(1-isobutoxyethoxy)propionate dissolved in 20 ml of toluene. Thereto was dropwise added slowly 7.0 ml (0.12 mole) of methanol with stirring, so that the internal temperature of the reaction system could be kept at 40° C. After the completion of the dropwise addition, the resulting mixture was stirred at 40° C. for 7 hours, at room temperature overnight and at 60° C. for 2 hours to give rise to a reaction. To the reaction mixture was added 20 ml of water, followed by stirring for 0.5 hour. The organic layer was separated. The water layer was subjected to extraction with 20 ml of toluene. The two organic layers were combined and washed with 20 ml of water and 20 ml of a saturated aqueous sodium chloride solution in this order. The washed solution was dried over anhydrous sodium sulfate and then subjected to vacuum distillation to remove the solvent, whereby was obtained 3.0 g (yield: 84.4%) of an oily title compound (diastereomixture).

$[\alpha]_D^{24.0}$: –37.6° (c=1.03, CHCl$_3$).

The IR and MS spectrum were identical with those of the compound obtained in Example 4.

REFERENCE EXAMPLE 8

Methyl (S)-2-Methyl-3-(1-isobutoxyethoxy)propionate

A catalytic amount of pyridinium para-toluenesulfonate was added to 5.9 g (0.05 mole) of methyl (S)-(+)-3-hydroxy- 2-methylpropionate. Thereto was dropwise added 5.5 g (0.055 mole) of isobutyl vinyl ether at room temperature. Then, stirring was conducted at room temperature for 4 hours to give rise to a reaction. Thereto was added 100 ml of toluene. The resulting mixture was washed with 50 ml of a 0.1% aqueous sodium hydroxide solution and 20 ml of water in this order. The washed material was subjected to vacuum distillation to remove the solvent, whereby was obtained 10.5 g (yield: 97.0.%) of an oily title compound (diastereomixture).

$^1$H-NMR (300 MHz, CHCl$_3$-d$_1$), δ: 0.91 (d, 6H, J=6.6 Hz), 1.18 (d, 3H, J=6.9 Hz), 1.27, 1.29 (d, 3H, J=5.4 Hz), 1.8–1.9 (m, 1H), 2.7–2.8 (m, 1H), 3.13, 3.17 (dd, 1H, J=6.6, 0.9 Hz), 3.31, 3.34 (dd, 1H, J=6.6, 0.6 Hz), 3.69 (s, 3H), 3.4–3.7 (m, 2H), 4.67, 4.69 (q, 1H, J=5.4 Hz); IR (neat): 1754 cm$^{-1}$ (CO); MS (GC–MS) m/e: 217 (M$^+$–1), 73 (base).

EXAMPLE 18

(S)-2-Methyl-3-(1-isobutoxyethoxy)-1-propanol

In 50 ml of toluene were suspended 5.5 g (0.025 mole) of the methyl (S)-2-methyl-3-(1-isobutoxyethoxy)propionate obtained in Reference Example 8 and 6.0 g (0.15 mole) of sodium borohydride. Thereto was dropwise added slowly 24.0 g of methanol with stirring while the internal temperature of the reaction system was kept at 60° C. or less, to give rise to a reaction. The reaction mixture was washed with 50 ml of water twice. The washed material was subjected to vacuum distillation to remove the solvent, whereby was obtained 3.8 g (yield: 80.0%) of an oily title compound (diastereomixture).

$^1$H-NMR (300 MHz, CHCl$_3$-d$_1$), δ: 0.90 (d, 6H, J=6.6 Hz), 0.94 (d, 3H, J=6.6 Hz), 1.31 (d, 3H, J=5.4 Hz), 1.8–1.9 (m, 1H), 1.9–2.1 (m, 1H), 2.57, 2.59 (d, 1H, J=11.1 Hz), 3.2–3.7 (m, 6H), 4.60, 4.65 (q, 1H, J=5.4 Hz); IR (neat): 3422 cm$^{-1}$ (OH); MS (GC–MS) m/e: 189 (M$^+$–1), 57 (base).

REFERENCE EXAMPLE 19

Isobutyl (R)-2-(Methoxymethoxy)propionate 2.0 g of 60% sodium hydride was suspended in 50 ml of toluene. The suspension was cooled on an ice bath. Thereto was dropwise added 7.3 g of isobutyl (R)-(+)-lactate with stirring, followed by stirring for 1 hour. Thereto was dropwise added 5.0 g of chloromethoxymethane, followed by stirring for 3 hours. The reaction mixture was washed with 50 ml of a saturated aqueous sodium hydrogen carbonate solution and 30 ml of water in this order. The washed material was subjected to vacuum distillation to remove the solvent, whereby was obtained 9.0 g (yield: 86.6%) of an oily title compound.

$^1$H-NMR (300 MHz, CHCl$_3$-d$_1$) δ: 0.93 (d, 6H, J=6.9 Hz), 1.43 (d, 3H, J=6.9 Hz), 1.95 (d, 1H, J=6.9 Hz), 3.38 (s, 3H), 3.92 (d, 2H, J=6.9 Hz), 4.24 (q, 1H, J=6.9 Hz), 4.67 (d, 1H, J=10.2 Hz), 4.70 (d, 1H, J=10.2 Hz); IR (neat): 1752 cm$^{-1}$ (CO); MS (GC–MS) m/e: 189 (M$^+$–1), 89 (base).

EXAMPLE 19

(R)-2-(Methoxymethoxy)-1-propanol

In 40 ml of pentane were suspended 5.2 g (0.025 mole) of the isobutyl (R)-2-(methoxymethoxy)propionate obtained in Reference Example 9 and 1.1 g (0.030 mole) of sodium borohydride. Thereto was dropwise added slowly 3.2 g of methanol with stirring while the internal temperature of the reaction system was kept at 30° C. or less, to give rise to a reaction. To the reaction mixture was added 80 ml of ether, followed by washing with 20 ml of water twice and 10 ml of brine once. The washed material was dried over anhydrous sodium sulfate and then subjected to vacuum distillation to remove the solvent, whereby was obtained 3.4 g (yield: 91.5%) of an oily title compound.

$^1$H-NMR (300 MHz, CHCl$_3$-d$_1$), δ: 1.15 (d, 3H, J=6.3 Hz), 2.85 (dd, 1H, J=8.4, 4.2 Hz), 3.39 (s, 3H), 3.4–3.6 (m, 2H), 3.7–3.8 (m, 1H), 4.68 (d, 1H, J=11.1 Hz), 4.71 (d, 1H, J=11.1 Hz); IR (neat): 3448 cm$^{-1}$ (OH); MS (GC–MS) m/e: 119 (M$^+$–1), 89 (base).

EXAMPLE 20

(R)-(–)-1,2-Propanediol

In 250 ml of toluene were placed 61.5 g (0.42 mole) of isobutyl (R)-(+)-lactate and 11.5 g (0.305 mole) of sodium borohydride. Thereto was dropwise added 54 g (1.69 moles) of methanol at room temperature with stirring so that the internal temperature of the reaction system could be kept at 40° C. or less. Stirring was conducted at room temperature and, after 2 hours, the disappearance of the raw material was confirmed by GC. To the reaction mixture was added 50 ml of methanol, and stirring was conducted at room temperature for 1 hour to deactivate the remaining sodium borohydride. To the reaction mixture was dropwise added a 35% aqueous hydrochloric acid solution for neutralization to pH 7.3. The resulting material was filtered through Celite. The toluene layer as filtrate was subjected to vacuum distillation. The residue was subjected to distillation at a boiling point of 111° C./5.3 KPa to obtain 18.3 g (yield: 78.9%) of (R)-(–)-1,2-propanediol.

$[\alpha]_D^{26}$: –21.9° (c=7.5, H$_2$O) [Reference Value in Synthesis, 142 (1984), $[\alpha]_D^{25}$: –20.1° (c=8, H$_2$O)].

The NMR and IR spectrum were identical with those of the standard racemic compound.

EXAMPLE 21

(S)-(+)-1,2-Propanediol

In 250 ml of cyclohexane were placed 44.4 g (0.42 mole) of methyl (S)-(–)-lactate (98.4% e.e) and 11.5 g (0.305 mole) of sodium borohydride. A reaction and a treatment were conducted in the same manner as in Example 20. By distillation was obtained 19.2 g (83%) of (S)-(+)-1,2-propanediol.

$[\alpha]_D^{20}$: +16.7° (neat).

The product was measured for optical purity by an HPLC using optically active column, which was 98.4% e.e.

COMPARATIVE EXAMPLE 1 (CARRIED OUT ACCORDING TO JP-A-1-250369)

(R)-(–)-2-(1-Isobutoxyethoxy)-1-propanol 4.9 g (0.12 mole) of sodium borohydride was suspended at room temperature in a solution of 24.9 g (0.10 mole) of isobutyl (R)-(+)-2-(1-isobutoxyethoxy)propionate dissolved in 100 ml of 1,2-dichloroethane. Thereto was dropwise added slowly 24.0 ml (0.60 mole) of methanol with stirring so that the internal temperature of the reaction system could be kept at 40° C. After the completion of the dropwise addition, the resulting mixture was stirred at room temperature with the disappearance of the raw material being monitored by GC, to give rise to a reaction. 20 hours were necessary. Then, 50 ml of water was added, followed by stirring for 0.5 hour. The organic layer was separated. The water layer was subjected to extraction with 50 ml of toluene. The two organic layers were combined and washed with 30 ml of water and 30 ml of a saturated aqueous sodium chloride solution in this order. The washed solution was dried over anhydrous sodium sulfate and then subjected to vacuum distillation to remove the solvent. The resulting concentrate was subjected to distillation to obtain 16.3 g (yield: 92.6%) of an oily title compound (diastereomixture).

$[\alpha]_D^{24.0}$: −37.9° (c=1.07, CHCl$_3$);

The IR and MS spectrum agreed with those of the compound obtained in Example 4.

COMPARATIVE EXAMPLE 2 (A REACTION IN A METHANOL SOLVENT)

Methyl (R)-(+)-2-(1-Isobutoxyethoxy)propionate 0.5 g (0.012 mole) of sodium borohydride was suspended in 10 ml of methanol at room temperature. Thereto was added 2.5 g (0.01 mole) of isobutyl (R)-(+)-2-(1-isobutoxyethoxy)propionate with stirring. The resulting mixture was stirred at room temperature for 6 hours but no change was seen. Therefore, the mixture was heated to 60° C. and stirred for 4 hours to give rise to a reaction. The crude reaction mixture was analyzed. As a result, the raw material remained by 7% and the main product included 92% of a title compound formed by conversion (ester exchange) of the raw material isobutyl ester to the corresponding methyl ester, and no 2-(1-isobutoxyethoxy)-1-propanol was detected. After the reaction, 20 ml of water was added, followed by stirring for 0.5 hour. Then, 50 ml of toluene was added and the organic layer was separated. The water layer was subjected to extraction with 20 ml of toluene. The two organic layers were combined and washed with 20 ml of water and 20 ml of a saturated aqueous sodium chloride solution in this order. The washed solution was dried over anhydrous sodium sulfate and then subjected to vacuum distillation to remove the solvent. The resulting concentrate was subjected to distillation to obtain 1.8 g (yield: 90.8%) of an oily methyl ester compound. The GC–MS spectrum of this compound agreed with that of the compound obtained in Reference Example 5.

What is claimed is:

1. A process for producing an alcohol derivative represented by the following general formula (II):

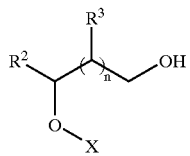

(II)

(wherein R$^2$ and R$^3$ are each independently a hydrogen atom or an alkyl group having 1 to 4 carbon atoms; X is a hydrogen atom or a protecting group for hydroxyl group which can be removed under an acidic condition; and n is 0 or 1), which process comprises reducing an ester compound represented by the following general formula (I):

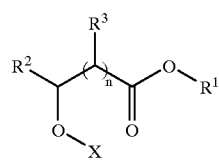

(I)

(wherein R$^1$ is an alkyl group having 1 to 4 carbon atoms; and R$^2$, R$^3$, X and n have the same definitions as given above) with sodium borohydride in a mixed solvent of at least one kind of solvent selected from the group consisting of aromatic hydrocarbons, aliphatic hydrocarbons and alicyclic hydrocarbons and methanol.

2. A process for producing an alcohol derivative represented by the following general formula (II):

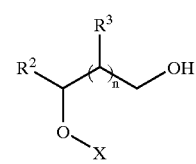

(II)

(wherein R$^2$ and R$^3$ are each independently a hydrogen atom or an alkyl group having 1 to 4 carbon atoms; X is a hydrogen atom, a substituted methyl group, or a substituted ethyl group; and n is 0 or 1), which process comprises reducing an ester compound represented by the following general formula (I):

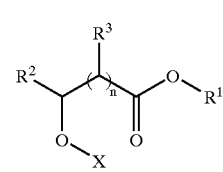

(I)

(wherein R$^1$ is an alkyl group having 1 to 4 carbon atoms; and R$^2$. R$^3$, X and n have the same definitions as given above) with sodium borohydride in a mixed solvent of at least one kind of solvent selected from the group consisting of aromatic hydrocarbons, aliphatic hydrocarbons and alicyclic hydrocarbons and methanol.

3. A process for producing an alcohol derivative represented by the following general formula (II):

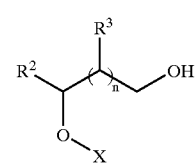

(II)

(wherein R$^2$ and R$^3$ are each independently a hydrogen atom or an alkyl group having 1 to 4 carbon atoms; X is a hydrogen atom or a protecting group for hydroxyl group which can be removed under an acidic condition; and n is 0 or 1), which process comprises reducing an ester compound represented by the following general formula (I):

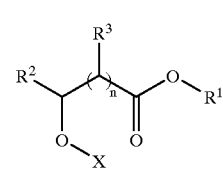

(I)

(wherein R$^1$ is an alkyl group having 1 to 4 carbon atoms; and R$^2$; R$^3$, X and n have the same definitions as given above) with sodium borohydride in a mixed solvent of at least one kind of solvent selected from the group consisting of aromatic hydrocarbons, aliphatic hydrocarbons and alicyclic hydrocarbons and methanol, at room temperature.

* * * * *